(12) United States Patent
Vidra et al.

(10) Patent No.: US 11,851,772 B2
(45) Date of Patent: Dec. 26, 2023

(54) COMPOSITION AND METHOD FOR CREATING NANOSCALE SURFACE GEOMETRY ON AN IMPLANTABLE DEVICE

(71) Applicant: TECH MET, INC., Glassport, PA (US)

(72) Inventors: Michael Vidra, Export, PA (US); Edward Palanko, New Stanton, PA (US); Robert Vaccaro, Greensburg, PA (US); Jordan Incerpi, Pittsburgh, PA (US)

(73) Assignee: Tech Met, Inc., Glassport, PA (US)

( * ) Notice: Subject to any disclaimer, the term of this patent is extended or adjusted under 35 U.S.C. 154(b) by 570 days.

(21) Appl. No.: 15/930,484

(22) Filed: May 13, 2020

(65) Prior Publication Data

US 2020/0362466 A1    Nov. 19, 2020

Related U.S. Application Data

(60) Provisional application No. 62/871,326, filed on Jul. 8, 2019, provisional application No. 62/847,407, filed on May 14, 2019.

(51) Int. Cl.
*C23F 1/40* (2006.01)
*A61L 31/02* (2006.01)
(Continued)

(52) U.S. Cl.
CPC ............. *C23F 1/40* (2013.01); *A61L 27/06* (2013.01); *A61L 27/365* (2013.01); *A61L 31/022* (2013.01); *C09K 13/02* (2013.01)

(58) Field of Classification Search
CPC ...... C23F 1/40; C23F 1/38; C23F 1/02; C23F 1/36; A61L 27/06; A61L 27/365;
(Continued)

(56) References Cited

U.S. PATENT DOCUMENTS 5,258,098 A    11/1993    Wagner et al.
5,507,815 A    4/1996    Wagner et al.
(Continued)

FOREIGN PATENT DOCUMENTS

JP    2011184595 A    *    9/2011    ............... C11D 3/60

OTHER PUBLICATIONS

Aperam, steel content (Year: 2022).*
(Continued)

*Primary Examiner* — Duy Vu N Deo
(74) *Attorney, Agent, or Firm* — Dentons Cohen & Grigsby P.C.

(57) ABSTRACT

Compositions and methods for etching a surface of an implantable device are disclosed. The compositions generally include one or more alkali components, such as a metal hydroxide and an amine, one or more chelating agents, and optionally iron (Fe) and/or certain component metals of the metal or alloy to be etched. For example, when etching a titanium device, the metals may include titanium (Ti). Alternatively, the composition may be an electrolyte composition useful for electrochemical etching of the implantable device. These compositions and methods may generate nanoscale geometry on the surface of the implantable device to provide implants with accelerate osseointegration and healing after surgery.

20 Claims, 2 Drawing Sheets

(51) Int. Cl.
A61L 27/06 (2006.01)
A61L 27/36 (2006.01)
C09K 13/02 (2006.01)

(58) Field of Classification Search
CPC ............... A61L 31/022; A61L 2400/12; A61L 2400/18; A61L 2430/02; A61L 2430/12; A61L 2430/20; A61L 2430/38; A61L 27/306; A61L 31/088; C09K 13/02; C25F 3/14; C25F 3/02; C25F 3/08
USPC ...................................................... 252/79.5
See application file for complete search history.

(56) References Cited

U.S. PATENT DOCUMENTS

| | | | |
|---|---|---|---|
| 6,193,762 | B1 | 2/2001 | Wagner et al. |
| 7,501,073 | B2 | 3/2009 | Wen et al. |
| 8,262,737 | B2 | 9/2012 | Bagga et al. |
| 8,496,710 | B2 | 7/2013 | Bagga et al. |
| 8,585,765 | B2 | 11/2013 | Ullrich, Jr. et al. |
| 8,878,146 | B2 | 11/2014 | Ogawa |
| 9,283,056 | B2 | 3/2016 | Mayfield et al. |
| 9,456,901 | B2 | 10/2016 | Jones et al. |
| 10,022,232 | B2 | 7/2018 | Mandanici et al. |
| 10,111,753 | B2 | 10/2018 | Patterson et al. |
| 2018/0057773 | A1* | 3/2018 | McMillen ............ C11D 3/0047 |
| 2019/0284704 | A1* | 9/2019 | Ge ............................ C23F 1/26 |

OTHER PUBLICATIONS

Baek, W, et al., Positive Regulation of Adult Bone Formation by Osteoblast-Specific Transcription Factor Osterix. J. Bone Miner. Res. (2009) 24(6):1055-65.

Zhang, C, et al., Transcriptional regulation of bone formation by the osteoblast-specific transcription factor Osx. Journal of Orthopaedic Surgery and Research (2010) 5(1):1.

Tu, Q, et al., Osterix Overexpression in Mesenchymal Stem Cells Stimulates Healing of Critical-Sized Defects in Murine Calvarial Bone. Tissue Eng. (2007) 13(10):2431-40.

Leung, K, et al., Plasma bone-specific alkaline phosphatase as an indicator of osteoblastic activity. Bone & Joint Journal (1993) 75-B(2):288-92.

Herrmann, M, et al., Different Kinetics of Bone Markers in Normal and Delayed Fracture Healing of Long Bones. Clinical Chemistry (2002) 48(12):2263-6.

Borden, M, et al., Tissue-engineered bone formation in vivo using a novel sintered polymeric microsphere matrix. J Bone Joint Surg Br. (2004) 86(8):1200-8.

Bancroft, G, et al., Fluid flow increases mineralized matrix deposition in 3D perfusion culture of marrow stromal osteoblasts in a dose-dependent manner. Proc. Natl. Acad. Sci. (2002) 99(20):12600-5.

* cited by examiner

COMPOSITION AND METHOD FOR CREATING NANOSCALE SURFACE GEOMETRY ON AN IMPLANTABLE DEVICE

CROSS-REFERENCE TO RELATED APPLICATIONS

The present application claims the benefit under 35 U.S.C. § 119(e) of prior U.S. Provisional Application Ser. No. 62/871,326, filed Jul. 8, 2019, and 62/847,407, filed May 14, 2019, the entire contents of which are incorporated herein.

TECHNICAL FIELD

This invention pertains generally to compositions and methods useful for creating nanoscale surface geometry on tissue-contacting and bone-contacting surfaces of implantable devices.

BACKGROUND

Tissue and blood contacting implants such as stents were developed to treat various vascular conditions and blockages and to provide an alternative to highly invasive, life-threatening surgeries, particularly in the treatment of coronary artery disease and blocked carotid arteries. A typical stent is a mesh-like tube used to support the vessel wall after minimally invasive treatments such as balloon angioplasty. In most cases, the metal stent is produced by a three-step process that includes laser cutting followed by chemical (acidic) etching and electropolishing.

The final electropolishing step is generally included to lessen restenosis, i.e., when the body coats the stent with scar tissue and relocks the treated vessel. The smooth surface enhances biocompatibility as it influences the amount of protein adherence, determined by the contact area of the stent with the artery. The smooth surface also eases insertion and travel through the tortuous vessel pathway prior to implantation, and reduces activation and aggregation of platelets, which is recognized as one component of the thrombosis process. As such, the surface properties of a stent determine post stent implantation complications like thrombogenicity and tissue reaction. The optimal stent is engineered to be highly deliverable, to inhibit vascular smooth muscle proliferation and generation of extracellular matrix proteins, and to enhance endothelial attachment, proliferation, and restoration of a healthy endothelial surface.

The optimal surface has been found to be absent micron-sized particles or surface geometry as this encourages neointimal tissue formation. Currently available stents, therefore, frequently include coatings such as hydroxyapatite or nanoporous aluminum oxide over a base material. These coatings provide a nano-sized geometry that has been found to enhance endothelial regeneration. These coatings, however, have been observed to eject nanoparticle debris that can trigger inflammation and subsequent restenosis. Thus, improved methods for providing a nanoscale geometry on tissue contacting surfaces of medical implants is an object of the present invention.

Bone contacting implants such as surgical bone fixation devices, i.e., wires, nails, screws, staples, rods, and plates, have been in clinical use for decades and have generally evolved from industrial designs for fastening wood, steel, plastic and other materials. Starting in the 1950s, Per-Ingvar Branemark and others demonstrated that implanted bone fixation devices made of pure titanium had the ability to become permanently incorporated with living bone tissue. That is, the living bone tissue becomes so fused with the titanium oxide layer of the implant that the two cannot be separated without fracture. Bone fixation devices formed from pure titanium and its various alloys are the basis for modern skeletal fixation techniques that support healing and functional repair of the human body.

As with tissue contacting devices, i.e., stents and valves, substantial data exists that strongly suggests manipulation of the material surface of a surgical bone fixation device can influence the rate and characteristics of the body's cellular response to the device, and thus the healing process. For example, differentiation of human bone marrow derived cells was found to accelerate on a titanium surface having a nanoscale surface geometry created by acid etching. Human mesenchymal stem cells, a small population of cells found in adult bone marrow, were found to express markers of an osteoblastic phenotype on an acid etched titanium surface to a greater level than on a non-etched titanium surface. Thus, titanium surfaces having a nanoscale surface geometry have been found to provide an improved substrate for bone growth and integration, i.e., osseointegration.

For implants having a titanium surface, for example, these desired surface features have typically been created by mechanical grit-blasting, by etching in solutions of acids, or by some combination of the two. The use of a strong acid to form these surface features is nearly universal. For example, titanium is typically etched through use of hydrofluoric acid or concentrated hydrochloric acid (HCl) at or near its boiling point.

Use of these acid-based etching solutions for either surface polishing or for the generation of nanoscale surface features has several drawbacks. For example, concentrated acids at elevated temperatures pose a significant safety risk to operators and the environment, e.g., through potential environmental emissions. The availability of suitable fabrication materials for the equipment used to complete these processes is significantly reduced, and equipment life is typically lessened as well. Moreover, use of acid solutions can also degrade the structural strength and performance of the native metal due to intergranular attack or through hydrogen pickup and subsequent embrittlement. The inclusion of HCl or other chloride-containing acid solutions compounds these issues further, with the associated susceptibility to interstitial chloride corrosion.

As previously mentioned, one particularly significant limitation of the high temperature acid solution approach is that the process typically takes place at or near the boiling point of the acid or the mixed acid solution (e.g., 20% HCl in $H_2O$ has boiling point of 110° C.). The desired chemical etch mechanisms that produce the targeted surface geometries do not typically occur at temperatures significantly below the boiling point and are not altered at temperatures significantly above. While this does provide a somewhat stable processing environment, it also limits the surface geometry. That is, the surface geometry is difficult to change with these types of chemistry since they require a very specialized and confined set of conditions for the geometry to form in the first place. Grit-blast conditions preceding the acid etching can alter the resulting etched surface to some extent, though its effects are limited.

Finally, given the harshness of the chemistry, the limited materials of construction, the precision of conditions required for the desired outcomes, the safety and environmental requirements, the necessity of batch processing due to volatility of the components at the operating temperatures, and the potential need for a preparatory grit blast process, the cost of processing by this means is understandably high.

Accordingly, there is need in the art for improved chemistries and methods for surface finishing of medical implants that may be safer and that may produce implants having improved biocompatibility and healing at the implant site.

SUMMARY

Described herein are alternate chemistries that address the major drawbacks of the prior art and allow for some adjustment or fine-tuning of surface feature geometries on a substrate. Accordingly, the present invention relates to compositions and methods useful for etching a nanoscale geometry on a metal or metal alloy surface, such as a surface of an implantable device.

According to certain aspects of the presently disclosed invention, the implantable device may be a tissue contacting device, such as a stent or valve (e.g., heart valve), wherein the nanoscale surface provided by the compositions and methods disclosed herein enhance biocompatibility and reduce complications like thrombogenicity and adverse tissue reaction. Enhanced biocompatibility may include enhanced endothelial attachment, proliferation, and restoration of a healthy endothelial surface, and reduced thrombogenicity and adverse localized tissue reaction.

According to certain other aspects, the implantable device may be a bone contacting device, wherein the nanoscale surface provided by the compositions and methods disclosed herein enhance osseointegration. Bone contacting implantable devices include any medical or dental implant for connection to, or positioning adjacent, a bone. For example, surgical bone fixation devices such as wires, nails, pins, screws, staples, rods, and plates, and in/plants including at least medical implants such as spinal implants, limb prostheses, cochlear prostheses, and dental implants are all implantable devices of the present invention.

According to aspects of the presently disclosed invention, the nanoscale geometry may be provided on a surface of any of the implantable devices disclosed herein through exposure to an etching composition.

According to certain aspects, the etching composition may be an alkaline etching composition generally comprising: one or more alkaline components; and one or more chelating agents. The composition may further include iron (Fe) and/or an additional component metal of the implantable device. According to certain aspects, the one or more alkaline components may comprise a metal hydroxide and an amine. The metal hydroxide may be included in the composition at 5 to 75 wt. %, such as 18 to 30 wt. %. The amine may be an alkanolamine and may be included in the composition at up to 40 wt. %, such as 2 to 10 wt. %. The one or more chelating agents may comprise a gluconate, which may be included in the composition at 0.1 to 40 wt. %, such as 2 to 10 wt. %. When included in the composition, iron may be provided at up to 10,000 ppm, or up to 5,000 ppm, or from about 70 ppm to about 180 ppm. When the implantable device includes a titanium surface that is to be etched, the additional component metal may include dissolved titanium at up to 100,000 ppm, such as up to 7,000 ppm. When the implantable device includes a surface having an alloy comprising aluminum that is to be etched, the additional component metal may include dissolved aluminum at up to 100,000 ppm, such as up to 7,000 ppm.

The presently disclosed invention further provides methods for chemically or electrochemically etching a surface of an implantable device, such as methods that may generate a nanoscale geometry on at least one surface thereof.

According to certain aspects, the methods generally include contacting at least one surface of the implantable device with the alkaline chemical etching composition. The step of contacting the at least one surface may be performed at a reaction temperature of about 60° F. to about 280° F. (about 15° C. to about 140° C.), such as about 175° F. to about 200° F. (about 80° C. to about 95° C.), for 1 minute to 100 hours, such as for 10 minutes to 60 minutes. The at least one surface may be contacted with the chemical etching composition for a time period that is unlimited and based on the depth to which the surface is to be etched, and/or the desired topological features (i.e., nanoscale geometry). According to certain exemplary aspects, the at least one surface may be contacted with the chemical etching composition for a time period of up to 1000 minutes, such as up to 200 minutes, or 100 minutes, or 50 minutes. According to certain exemplary aspects, the metal or metal alloy material may be etched for a time period of up at least 1 minute, or at least 2 minutes, or 5 minutes, or 10 minutes. Upper- and lower-time limits may be combined such as, for example, to provide an etch time of 1 to 1000 minutes or 5 to 50 minutes.

According to certain aspects, the surface of the implantable device may be etched electrochemically to generate the nanoscale surface geometry on at least a portion of an implantable device. The method generally comprises submerging the implantable device in an aqueous electrolyte solution, i.e., electrochemical etchant, wherein the aqueous electrolyte solution comprises 0.01M to 10M of one or more metal salts; and passing an electric current of 5 Amps/in$^2$ to 100 Amps/in$^2$ through the electrolyte solution between a cathode and an anode, wherein the implantable device acts as the anode or is connected to the anode. The one or more metal salts may be selected from sodium bromide (NaBr), sodium chloride (NaCl), sodium fluoride (NaF), potassium bromide (KBr), potassium chloride (KCl), potassium fluoride (KF), calcium chloride ($CaCl_2$)), magnesium chloride ($MgCl_2$), ammonium chloride ($NH_4Cl$), dibasic sodium phosphate ($Na_2HPO_4$), monobasic sodium phosphate ($NaH_2PO_4$), monobasic potassium phosphate ($KH_2PO_4$), dibasic potassium phosphate ($K_2HPO_4$), sodium sulfate ($Na_2SO_4$), potassium sulfate ($K_2SO_4$), ammonium sulfate (($NH_4)_2SO_4$) sodium nitrate ($NaNO_3$), potassium nitrate ($KNO_3$), ammonium nitrate ($NH_4NO_3$), potassium nitrite ($KNO_2$), and mixtures thereof.

According to certain aspects of the presently disclosed invention, any of the disclosed methods may include applying a coating which resists chemical or electrochemical etchants to the implantable device; removing a portion of the coating to form a patterned design in the coating on the implantable device or to expose a surface on the implantable device; and applying the chemical or electrochemical etching composition according to any of the aspects disclosed herein. According to certain aspects, the method may further comprise stripping the coating from the implantable device after etching is complete. For the chemical and electrochemical etching methods, the coating may be resistant to the chemical etching composition or may be electrically non-conductive, respectively.

The disclosed invention further provides implantable devices having a defined three-dimensional pattern produced using any of the methods and etching compositions disclosed herein. These surfaces may have improved biocompatibility and/or osseointegration and may provide improved healing at the implant site.

BRIEF DESCRIPTION OF THE DRAWINGS

Aspects, features, benefits and advantages of the embodiments herein will be apparent with regard to the following description, appended claims, and accompanying drawings.

FIGS. 2A-2C illustrate the surface of a standard commercially available titanium medical implant (control) treated with an etching composition according to various aspects of the presently disclosed invention, wherein FIGS. 2A-2C show scanning electron micrograph images at 500×, 1000×, and 2000× magnifications, respectively, of the surface.

FIGS. 3A-3C illustrate the surface of a titanium medical implant treated with an etching composition according to various aspects of the presently disclosed invention, wherein FIGS. 3A-3C show scanning electron micrograph images at 500×, 1000×, and 2000× magnifications, respectively, of the surface.

FIGS. 4A-4C illustrate the surface of a standard commercially available titanium medical implant (control), wherein FIGS. 4A-4C show scanning electron micrograph images at 500×, 1000×, and 2000× magnifications, respectively, of the surface.

DETAILED DESCRIPTION

Figure 1A:
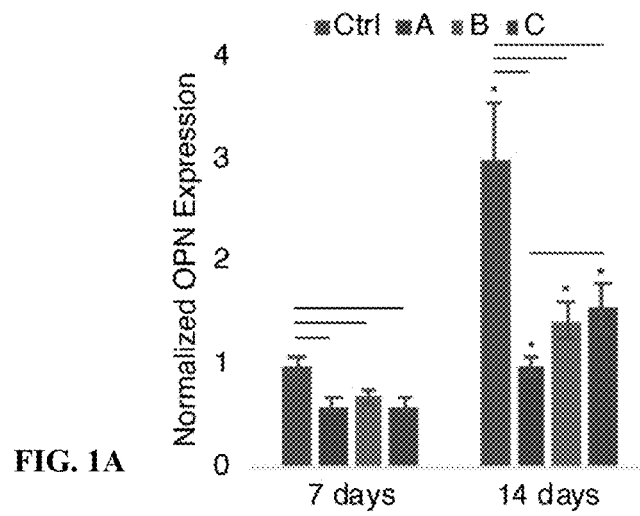
FIGS. 1A-1C illustrate expression levels for early (ALP), lifetime (OPN), and late (OCN) osteoblast protein markers for mesenchymal stem cells grown on control substrates and substrates having a nanoscale surface formed by methods and compositions according to various aspects of the presently disclosed invention.

In the following description, the present invention is set forth in the context of various alternative embodiments and implementations involving novel chemistries and methods for generating nanoscale geometry on titanium, titanium alloy, aluminum, and aluminum alloy surfaces. These novel chemistries and methods are useful for generating nanoscale geometry on tissue and bone contacting surfaces of medical implants. Moreover, medical implants produced using the compositions and methods disclosed herein have improved biocompatibility and healing at the implantation site. While the following description discloses numerous exemplary embodiments, the scope of the present patent application is not limited to the disclosed embodiments, but also encompasses combinations of the disclosed embodiments, as well as modifications to the disclosed embodiments.

Various aspects of the novel chemistry and methods disclosed herein may be illustrated by describing components that are coupled, attached, and/or joined together, or method steps that are linked. As used herein, the terms "coupled", "attached", "linked", and/or "joined" are interchangeably used to indicate either a direct connection between two components or method steps or, where appropriate, an indirect connection to one another through intervening or intermediate components or steps. In contrast, when a component is referred to as being "directly coupled", "directly attached", "directly linked", and/or "directly joined" to another component or method step, there are no intervening elements or steps shown in said examples.

Various aspects of the novel chemistry and methods disclosed herein may be described and illustrated with reference to one or more exemplary implementations. As used herein, the term "exemplary" means "serving as an example, instance, or illustration," and should not necessarily be construed as preferred or advantageous over other variations of the devices, systems, or methods disclosed herein. "Optional" or "optionally" means that the subsequently described event or circumstance may or may not occur, and that the description includes instances where the event occurs and instances where it does not. In addition, the word "comprising" as used herein means "including, but not limited to".

It must also be noted that as used herein and in the appended claims, the singular forms "a", "an", and "the" include the plural reference unless the context clearly dictates otherwise. For example, although reference is made to "a" metal, "an" alkaline component, and "the" substrate, one or more of any of these components and/or any other components described herein can be used.

Moreover, other than in any operating examples, or where otherwise indicated, all numbers expressing, for example, quantities of ingredients used in the specification and claims are to be understood as being modified in all instances by the term "about". Accordingly, unless indicated to the contrary, the numerical parameters set forth in the following specification and appended claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

"Substantially free", as used herein, is understood to mean inclusive of only trace amounts of a constituent. "Trace amounts" are those quantitative levels of a constituent that are barely detectable and provide no benefit to the functional properties of the subject composition, process, or articles formed therefrom. For example, a trace amount may constitute 1.0 wt. %, 0.5 wt. %, 0.1 wt. %, 0.05 wt. %, or even 0.01 wt. % of a component or constituent of any of the alkaline chemistries disclosed herein. "Totally free", as used herein, is understood to mean completely free of a component or constituent.

As used herein, the terms "implantable device", "device", and "substrate" may be used interchangeably, and may be understood to include any device that is either partly or totally introduced, surgically or medically, into the body of a mammal, such as a human, dog, cat, cow, pig, etc., and is intended to remain there after the procedure. The implantable device may be implanted to replace or repair a part or portion thereof that has worn-out, such as a heart valve or replacement joint, or may be used to ameliorate a condition of the mammal that may benefit for insertion of the implantable device such as a stent. The implantable device may also be useful for sensing a physiological response in vivo or to actuate physiological organs, such as an implantable cardiac defibrillator, pacemaker, cochlear implant, implanted bladder stimulator, implantable wireless pressure sensor, etc.

As used herein, the phrase "defined three-dimensional pattern" generally refers to a nanoscale surface geometry imparted by the chemical etching compositions and methods of the present invention "Nanoscale surface geometry", as used herein, is understood to mean a surface having topological features with sizes dimensions in the nanoscale range, such as from 1 nm to 5,000 nm, or from 10 nm to 3,000 nm, or from 20 nm to 2,000 nm.

The nanoscale surface geometry of the present invention, when formed on a surface of an implantable device, may enhance the biocompatibility of the device. As used herein, the term "biocompatible" may be understood to mean that the implanted device may have a medically acceptable degree of biocompatibility, i.e., that the device does not induce, or lessens, undesirable side effects within the body of the recipient. These undesirable side effects include blood clotting, tissue death, tumor formation, allergic reactions, foreign body reaction (rejection) and/or inflammatory reactions.

Unless defined otherwise, all technical and scientific terms used herein have the same meanings as commonly understood by one of ordinary skill in the art.

Novel etch chemistries and methods have been developed to address the major drawbacks of the prior art acid etch chemistries, and to allow for adjustment or fine-tuning of surface feature geometries. The novel chemistries and methods disclosed herein are safer to use, easily scalable, environmentally benign, and allow for a wider material selection for the equipment used in the process. Additionally, the chemical etch compositions are generally non-acidic and chloride free, while the electrochemical etch compositions are generally used at room temperature, both of which greatly reduce the rates of hydrogen pickup, potential embrittlement, and other corrosion of the substrate.

The compositions disclosed herein provide a means for performing a subtractive process on a substrate surface, i.e., chemical or electrochemical etching, also referred to as chemical or electrochemical machining or milling. Chemical etching may comprise, for example, exposure of select surfaces of an object or implantable device, or the entire implantable device, to the chemical etching compositions disclosed herein for a period of time sufficient to remove a portion of the surface to form the desired topographical features (i.e., nanoscale topology). In electrochemical etching, an electric circuit is established with a suitable cathode fixed at a desired distance from the substrate or surface, which acts as the anode. An electrolyte compatible with both anode and cathode materials is introduced between the cathode and anode, and current is passed through the circuit. Metal ions from the exposed portions of the substrate or surface are dissolved or dislocated into the electrolyte at a rate proportional to the current applied.

The presently disclosed compositions have relatively low volatility, and so maintain a stable operation over time with little adjustment necessary. Moreover, emissions from the processes are generally environmentally benign and unrestricted. For example, environmental emissions from the chemical etch process are primarily hydrogen, which may be vented for potential safety reasons.

Metals and Metal Alloys

The etching compositions and methods disclosed herein may be used to etch a wide range of metals. Exemplary metals include at least titanium, aluminum, and alloys thereof. When included as all or part of an implantable device, the metals may be those that are biocompatible. As such, the metal components or implantable devices having surfaces etched using the compositions and methods disclosed herein generally have at least an outer layer including titanium or a titanium alloy.

Metals and metal alloys useful as substrates in the methods of the present invention include at least titanium or a titanium-based alloy. Suitable titanium alloys include, but are not limited to, titanium-aluminum alloys such as the titanium-3-aluminum-2.5-vanadium alloy (Ti-3Al-2.5V) described in, for example, ASTM Standard F2146-01 and the titanium-6-aluminum-4-vanadium (Ti-6Al-4V) alloy described in, for example, ASTM Standard F136-02a. ASTM standards are available in print or electronic media from ASTM International (West Conshohocken, Pa.).

A titanium-zirconium alloy, i.e., Straumann Roxolid, comprising 13%-17% zirconium (TiZr13-17) is found to have better mechanical attributes, such as increased elongation and fatigue strength, than pure titanium and may also provide an excellent substrate for use as an implantable device as disclosed herein.

Chemical Etching Compositions and Methods

The chemical etching compositions of the presently disclosed invention broadly comprise one or more alkaline components, combined with one or more complexing or chelating agents. According to certain aspects, the compositions may further include one or more dissolved metals in solution to moderate and stabilize the rate of reaction.

According to certain aspects, the present invention provides an alkaline composition for etching a substrate comprising a metal hydroxide, an amine, one or more chelating agents, and dissolved metals, such as iron (Fe) and/or other component metals found in the substrate. For example, when etching a titanium substrate, the dissolved metals may include dissolved titanium, and when etching an aluminum substrate, the dissolved metals may include dissolved aluminum.

The metal hydroxides, such as sodium hydroxide and potassium hydroxide, may be included in the etch compositions at from 5 to 75 wt. %, based on the total weight of the composition. According to certain aspects, the metal hydroxide may be included in the composition in an amount of at least 5 wt. %, such as 10 wt. %, or 15 wt. %, or 18 wt. %, or 20 wt. %. According to certain aspects, the metal hydroxide may be included in the composition in an amount of up to 75 wt. %, or up to 65 wt. %, or up to 55 wt. %, or up to 45 wt. %, or up to 35 wt. %, or up to 30 wt. %. According to certain aspects, the metal hydroxide may be included in the composition at from 18 wt. % to 30 wt. %.

In addition to the metal hydroxides, the compositions generally comprise an amine or mixture of amines, such as an alkanolamine or mixture thereof. Exemplary alkanolamines include at least triethanolamine, diethanolamine, ethanolamine, and mixtures such as triethanolamine and diethanolamine. According to certain aspects, the amine(s) may be included in the composition at 0.1 wt. % to 40 wt. %. The amine(s) may be included in the composition at up to 40 wt. %, such as up to 35 wt. %, or up to 30 wt. %, or up to 25 wt. %, or up to 20 wt. %, or up to 15 wt. %, or up to 10 wt. %, or up to 6 wt. %. The amine(s) may be included in the composition in an amount of at least 0.01 wt. %, or at least 0.1 wt. %, or at least 1 wt. %, or at least 2 wt. %, or at least 3 wt. %. The amine(s) may be included in the composition at from 2 wt. % to 10 wt. %, or even from 3 wt. % to 6 wt. %.

The chemical etching compositions further comprise one or more chelating agents, such as a gluconate. An exemplary gluconate includes at least sodium gluconate. According to certain aspects, the one or more chelating agents may be included in the composition at 0.1 wt. % to 40 wt. %, such as 2 to 10 wt. %, or even 3 to 6 wt. %. The chelating agents may be included in the composition at up to 40 wt. %, such as up to 35 wt. %, or up to 30 wt. %, or up to 25 wt. %, or up to 20 wt. %, or up to 15 wt. %, or up to 10 wt. %, or up to 6 wt. %. The chelating agents may be included in the composition in an amount of at least 0.01 wt. %, or at least 0.1 wt. %, or at least 1 wt. %, or at least 2 wt. %, or at least 3 wt. %. The chelating agents may be included in the composition at from 2 wt. % to 10 wt. %, or even from 3 wt. % to 6 wt. %.

According to aspects of the present invention, the composition comprises component metals of the metal or metal alloy to be etched. For example, the chemical etching solution may comprise titanium (Ti) when used to etch a titanium substrate or implantable device. The component metal(s) may be included in the composition at up to 100,000 ppm, such as up to 7,000 ppm, or from about 100 ppm to about 7,000 ppm. According to certain aspects, the component metals may be included in the composition an amount of up to 100,000 ppm, or up to 20,000 ppm, or up to 10,000 ppm, or up to 7,000 ppm. According to certain aspects, the component metals may be included in the composition an amount of at least 1 ppm, or at least 10 ppm, or at least 50 ppm, or at least 100 ppm, or at least 500 ppm, or at least 1,000 ppm.

The composition may further comprise iron (Fe). Without being tied to one particular theory, it is believed that the addition of iron to the composition may help stabilize the reaction rate of the composition and increase its longevity (i.e., increase the number of implantable devices that can be etched before having to change the solution). Iron may be included in the chemical etching compositions at up to 10,000 ppm, such as up to 5,000 ppm, or up to 500 ppm, or from about 70 to about 180 ppm. According to certain aspects, iron may be included in the composition an amount of up to 10,000 ppm, or up to 5,000 ppm, or up to 2,000 ppm, or up to 1,000 ppm, or up to 100 ppm. According to certain aspects, iron may be included in the composition an amount of at least 1 ppm, or at least 10 ppm, or at least 50 ppm, or at least 70 ppm, or at least 100 ppm.

According to certain aspects of the present invention, the total amount of metal(s) included in the composition may be at least 100 ppm from either of the iron or component metals of the metal or metal alloy to be etched. That is, if at least 100 ppm of the component metal is included (e.g., 100 ppm titanium or aluminum), the composition may include no iron. Alternatively, if at least 100 ppm of iron is included in the composition, the component metal may be optional (e.g., 0 ppm titanium or aluminum).

An exemplary alkaline etching composition comprises one or more alkaline components; one or more chelating agents; optionally iron (Fe); and optionally, an additional component metal of the implantable device. According to certain aspects, the one or more alkaline components may comprise a metal hydroxide and an amine. The metal hydroxide may be included in the composition at 5 to 75 wt. %, such as 18 to 30 wt. %. The amine may be an alkanolamine and may be included in the composition at up to 40 wt. %, such as 2 to 10 wt. %. The one or more chelating agents may comprise a gluconate, which may be included in the composition at 0.1 to 40 wt. %, such as 2 to 10 wt. %. The metals may optionally include iron, such as up to 10,000 ppm, or up to 5,000 ppm, or from about 70 ppm to about 180 ppm, and optionally additional component metals of the implantable device, such as up to 100,000 ppm, or up to 7,000 ppm.

The metal component or implantable device may be exposed to the inventive chemical etching compositions at temperatures of about 60° F. to about 280° F. (about 15° C. to about 140° C.), such as about 175° F. to about 200° F. (about 80° C. to about 95° C.), for time periods of up to 100 hours, such as at least 1 minute to 10 hours, or from 10 minutes to 60 minutes.

The process itself is both very stable and highly repeatable. The chemistry is compatible with a much wider range of construction materials than prior art acid etch compositions, as long as the operating temperature is accounted for (e.g., 316 stainless steel is an example of a common material that is an appropriate choice for use in the processing equipment and provides a long equipment life).

Further, the combination of the improvements above make this process and chemistry readily scalable and easy to automate. The alkaline etching chemistry is also very stable and provides a highly repeatable means for etching a nanoscale geometry into the surface of a titanium or aluminum substrate, such as a surface of an implantable device. Thus, processing costs using the novel compositions and methods disclosed herein are lower than prior art acid etch compositions and methods.

The chemical etching compositions and methods of the present invention may be used to etch a metal substrate, such as a titanium, titanium alloy, or aluminum alloy substrate, leaving a surface having nanoscale geometry. As mentioned, these inventive compositions and methods allow fine adjustment of the surface geometry by varying the amounts of various components in the composition, and/or the time and temperature of exposure, either in unison or relative to one another. That is, the concentrations of the various components may be raised in unison, such as by addition of components or evaporation; lowered in unison, such as by addition of aqueous solvent; or changed individually. Additionally, the time and temperature of exposure may be varied with changes in the chemistry, or with changes in either of the variables (e.g., increased exposure time at lowered reaction temperatures).

Accordingly, the metal or metal alloys disclosed herein may be included as a surface of an implantable device, such as a surface formed over another material such as a ceramic or polymeric material, or may form the entirety of the implantable device, wherein the methods and composition of the present invention may be used to form a nanoscale geometry on that surface.

According to certain aspects of the present invention, the implantable device may be etched on one or more surfaces by contacting the device with an etching composition as disclosed herein. Contacting the implantable device with the alkaline chemical etching compositions may include dipping or submersing the device in the composition, or spraying, rolling, or brushing the composition onto one or more surfaces of the implantable device. For example, the part to be etched may be attached to a fixture resistant to the chemical etch composition and both the part and at least a portion of the fixture may be submerged in the chemical etch composition for a specified time (e.g., the part is suspended over/in the chemical etch composition).

According to certain aspects, the surfaces to be etched horizontally, such as facing upward in the solution, or vertically depending on the targeted surface characteristics. Thus, according to certain aspects of the present invention, the implantable device may be etched on one or more surfaces by positioning the device at an angle within the chemical etching composition. Exemplary angles include 0° with respect to the surface of the "bath" containing the chemical etch composition (i.e., horizontal facing upward), to 90° with respect to the surface of the bath (i.e., vertical), to 180° with respect to the surface of the bath (i.e., horizontal facing downward), or any angle therebetween.

Alternatively, the part may be placed into a drum filled with the chemical etch composition, and the drum may be rotated. Additional substrate, such as inert plastic beads or pieces, may be added to the drum to cushion the parts during rotation.

The chemical etching step may include agitating the implantable device in the chemical etching composition (e.g., using the rotating drum discussed above, or by agitating the fixture that is attached to the part). The chemical etching step may include recirculating the etching composition, wherein the recirculating may include circulation of the original chemical etching solution (i.e., etching solution applied/used at start of method), or circulation of the original chemical etching solution with additional new, unused chemical etching solution. The chemical etching step may include exchange of used chemical etching solution after a certain amount of etch time for new, unused chemical etch solution.

The chemical etching step may further include heating the implantable device and/or the chemical etching composition to a temperature in a range of from about 60° F. (about 15° C.) to about 280° F. (about 140° C.), such as from about 90° F. (about 32° C.) to about 250° F. (about 120° C.), or from about 150° F. (about 65° C.) to about 225° F. (about 110° C.), or from about 175° F. (about 80° C.) to about 200° F. (about 95° C.). According to certain aspects, the metal material of the implantable device may be contacted with the chemical etching composition at a temperature in a range of from about 60° F. (about 15° C.) to about 280° F. (about 140° C.), such as from about 90° F. (about 32° C.) to about 250° F. (about 120° C.), or from about 150° F. (about 65° C.) to about 225° F. (about 110° C.), or from about 175° F. (about 80° C.) to about 200° F. (about 95° C.).

The chemical etching methods may be used to remove portions or all of a surface of the implantable device to form the desired nanoscale topological features. Moreover, the compositions and methods disclosed herein provide removal of the material without significant intergranular attack (IGA). The compositions and methods disclosed herein also provide means to remove artifacts of manufacture, such as support structures formed during 3D manufacture of the implantable device, or islands left behind during laser manufacture of an implantable device, or to reduce debris from the implantable device surfaces, such as artifacts of the additive manufacturing process, e.g., powder, particles, granules, etc., that were not completely melted or completely sintered during the additive building. Debris may also include external debris such as dirt or other artifacts of handling.

An optional final step in the chemical etching methods of the presently disclosed invention includes exposing the etched device or surface to a nitric acid solution for a short time at about room temperature, i.e., a nitric flash. The nitric acid solution may be an aqueous solution comprising at least 5% (v/v) nitric acid, such as at least 10%, or at least 15%, or at least 20%. The nitric acid solution may be an aqueous solution comprising up to 60% (v/v) nitric acid, such as up to 50%, or up to 40%, or up to 30%, or up to 20%, or up to 15%. According to certain aspects, the nitric acid solution may be an aqueous solution comprising 5% to 15% (v/v) nitric acid, such as 10% to 12% (v/v).

The surface or device may be exposed to the nitric acid solution for 1 second to 10 minutes, such as 1 second to 5 minutes, at from 60° F. to 90° F. (about 15° C. to 32° C.). In an exemplary treatment step, the surface or device is exposed to an aqueous nitric acid solution comprising 10% to 12% (v/v) nitric acid for 90 seconds at room temperature (about 25° C.; 75° F.).

Prior to this exposure step, the alkaline etched surface or device is typically rinsed, such as with deionized water at about room temperature, e.g., between 25° C.-38° C. Moreover, the surface or device may also be rinsed, such as with deionized water at about room temperature, e.g., between 25° C.-38° C., after the nitric acid treatment. This treatment may be used to remove any staining, oxidation, and/or smut from the alkaline etch process. That is, the nitric flash may act as a de-smutting step to remove any of the less soluble aluminum or vanadium from the alkaline etch process performed prior to this step.

Electrochemical Etching Compositions and Methods

An electrochemical etching (EChE) process may be used to provide the nanoscale surface geometry. The device may be submerged in an electrolytic solution and may have a cathode inserted in the solution such that the cathode does not make contact with the device. The electrically conductive device may thus act as the anode, such that when an electric current passes through the electrolyte (between the anode and cathode), the surface of the device is etched, i.e., the current will etch the exposed surface by "plating" the device material, acting as the anode in this case, toward the inserted cathode in an electrochemical etching process. The device may be made electrically conductive by attachment to an anode (i.e., wired in a circuit)

The cathode may be shaped to match the general contour of the surface to maintain constant distance and therefore constant resistance between the cathode and anode, or a simple geometric shaped cathode such as a cylinder may be used and compensated with an insulating coating or cover applied selectively to achieve constant resistance across the cathode-anode gap. Fine tuning of the concentration of electrolyte, current, and temperature may be used so that a standard shaped cathode may remove material in a specific and selected manner.

According to certain aspects of the present invention, the device and the cathode may be placed into a fixture having electrical connection(s) (i.e., electric leads that make contact with or are directly attached to the device and the cathode). The electrolyte solution may be pumped into and through the fixture so that there is a flow of electrolyte solution between the device (i.e., anode) and the cathode (i.e., the anode-cathode gap). According to certain aspects, the cathode may be part of the fixture such that only the implantable device needs to be positioned within the fixture.

In all cases, the electrolyte solution may be recirculated or circulated so that newly introduced electrolyte may be moved rapidly through the anode-cathode gap and out into an external tank so that the removed material flows out into a settling tank instead of plating to the inserted cathode. Alternatively, the removed material may simply be plated onto the cathode.

Thus, according to certain methods of the presently disclosed invention, the device is exposed to an electrolyte solution comprising an aqueous solution having an electrolyte dissolved therein. The electrolyte may be selected from the group consisting of a water-soluble inorganic compound, a water-soluble organic compound, an acid, a base, a water-soluble oxidizer, an alcohol, a glycol, a glycol ether, an amine, an amide, a pyrrolidone, and mixtures thereof.

According to certain aspects, a preferred electrolyte solution is one that comprises a water-soluble inorganic compound. Any suitable water-soluble inorganic compound can be used to form the electrolyte solution. Suitable water-soluble inorganic compounds include salts of Group Ia, IIa, transition metals, and mixtures thereof. Examples of suitable metal cations include; lithium, sodium, potassium, magnesium, and calcium. According to certain aspects, the water soluble inorganic compound may be selected from the group consisting of chlorides, such as sodium chloride (NaCl), potassium chloride (KCl), calcium chloride ($CaCl_2$)), magnesium chloride ($MgCl_2$), and ammonium chloride ($NH_4Cl$); phosphates, such as dibasic sodium phosphate ($Na_2HPO_4$), monobasic sodium phosphate ($NaH_2PO_4$), monobasic potassium phosphate ($KH_2PO_4$), and dibasic potassium phosphate ($K_2HPO_4$); sulfates such as sodium sulfate ($Na_2SO_4$), potassium sulfate ($K_2SO_4$), and ammonium sulfate (($NH_4)_2SO_4$); nitrates such as sodium nitrate ($NaNO_3$), potassium nitrate ($KNO_3$), ammonium nitrate ($NH_4NO_3$), and potassium nitrite ($KNO_2$); bromides such as potassium bromide (KBr), sodium bromide (NaBr), ammonium bromide ($NH_4Br$), calcium bromide ($CaBr_2$), and magnesium bromide ($MgBr_2$); fluorides such as sodium fluoride (NaF), potassium fluoride (KF), and lithium fluoride (LiF), magnesium fluoride ($MgF_2$), and calcium fluoride ($CaF_2$); and mixtures thereof. Preferred electrolytes include NaCl, NaBr, NaF, KBr, KF, and KCl. Typically, the water soluble inorganic compound is present in the electrolyte solution at a concentration of about 0.01 M to saturation, such as from about 0.05 M to about 5 M, a concentration of about 0.05 M to about 3 M, or even at a concentration of about 0.1 M to about 1 M.

Water soluble organic compounds can be used in preparing the electrolyte solution. Suitable water soluble organic compounds include carbohydrates, including; tetroses such as erythrose, threose, and erythrulose; pentoses, such as ribose, arabinose, xylose, lyxose, ribulose, and xylulose; hexoses, such as allose, altrose, glucose, mannose, gulose, idose, galactose, talose, psiscose, fructose, sorbose, and tagatose; disaccharides, such as sucrose, lactose, maltose, trehalose, and cellobiose; oligosaccharides; polysaccharides; and mixtures thereof. In a preferred embodiment, the water-soluble organic compound is glucose. Typically, the water-soluble organic compound is present in the electrolyte solution at a concentration of about 0.0 M to about 5 M, preferably a concentration of about 0.05 M to about 3 M, and more preferably at a concentration of about 0.1 M to about 1 M.

The current and current density may be varied as well as the distance between the anode and the cathode, concentration and temperature of electrolytes, and flow rate of the electrolyte. This allows for optimization of a surface to maximize cellular response and the rate of bone integration through manipulation of these various factors. By such manipulation, it is possible to create surface geometries significantly superior to those of the prior art.

That is, a current may be applied and surface characteristics such as feature height, length and surface density (number of features in a given area) can be manipulated by adjustment of these various parameters. For example, the electrolyte type, i.e., salt solution, acid, alkaline, alcohol, or combinations of the preceding, and the electrolyte concentration may affect characteristics (i.e., total depth, pattern, geometry) of the etched surface. According to a preferred embodiment, the electrolyte may be a salt solution, such as a salt solution having some level of acidity (e.g., aqueous solutions of NaCl, NaBr, NaF, KBr, KF, or KCl). In addition, the presence of other organic and/or inorganic additives can directly impact the desired features and their generation on the surface.

As mentioned, the current, current density (rate of metal removal), and voltage may be varied, in addition to the temperature of the electrolyte solution. Such variation may affect the rate and amount of metal removal from the surface of the device. For example, the surface may be milled or removed to a depth of several mil (where 1 mil equals 25,400 nm). Additionally, the flow rate of the electrolyte, flow path of the electrolyte (e.g., flow direction, such as from the anode to the cathode or vice versa, or perpendicular to the plane of the anode and cathode, etc.), and the rate of recirculation of old electrolyte versus addition of new electrolyte may all affect the rate, pattern, and amount of material removed from the surface of the device. Other aspects, such as whether the electrical current is continuous or pulsed (direct) or pulsed (reversing), and the pulse period and duration may also affect the etch characteristics (e.g., surface geometry and pattern).

Finally, the surface design of the cathode tool (e.g., surface roughness, surface features, surface curvature, etc.), and the distance between the electrodes (i.e., the electrolyte gap; from thousandths of an inch to a gap measured in inches) may be varied to change the etch characteristics.

One embodiment that achieves many of the desired surface characteristics on both Grade 2 and Grade 5, and similar alloys, of titanium includes a mixture of one or more of NaCl, NaBr, NaF, KCl, KBr, KF. For example, in an exemplary embodiment, from 0.5 M to 5 M of each of NaCl, NaBr, and NaF are included in water to form an aqueous electrolyte solution. In a specific exemplary embodiment, the electrolyte solution may comprise NaCl (1.5 lb./gal, about 3 M), NaBr (1.0 lb./gal, about 1.2 M), and NaF (0.02 lb./gal, about 0.06 M) dissolved in deionized water.

The etching process is carried out by submersing the device in the electrolyte solution and passing a current between the cathode and the anode. The device may act as the anode, such as by connection of the anode to the device and positioning of the cathode in the electrolyte solution. The cathode may be positioned a specific distance from the device, i.e., an electrolyte gap. According to certain aspects, the electrolyte gap may be 0.05 to 1 inch (about 1.25 to 25.4 mm), such as 0.1 to 0.5 inches wide (about 2.54 to about 12.7 mm).

The electrochemical etching process is generally carried out at or near room temperature, such as from 15° C. to 30° C., or from 20° C. to 25° C., but elevated or reduced temperatures are also possible. The process may include use of a current density of from 5 to 100 DC Amps/$in^r$ surface, and a voltage of 5 to 20 V DC, generally non-pulsed. The electrolyte flow rate, direction and path may vary depending on the product design. In general, a 98+% first pass separation of byproducts from electrolyte can be expected during recirculation of the electrolyte solution.

The amount of metal removed from the surface, i.e., depth of etch, is unlimited, but generally less than about 10 mil (about 254,000 nm), such as less than about 5 mils (about 127,000 nm), or about 0.01 mils to about 5 mils (about 254 nm to about 127,000 nm) and may depend on the amount of exposure time and current, as well as the flow rate and temperature of the electrolyte solution. The depth of the etch is different from the nanoscale topology created by the novel chemistry and methods disclosed herein.

Pattern Generation

According to certain aspects of the present invention, portions of the implantable device may be etched, such as in a pattern. Those portions that are to remain un-etched may be protected from the etching composition using a masking material. Masking materials may include static adhesion films applied to the surfaces to be protected from the chemical etching compositions. Other masking materials may include at least coatings applied to the surfaces to be protected. The exposed, non-masked surfaces may then be etched by exposure to the etching compositions of the present invention.

For objects which are to be etched using a chemical etchant, the coating may be a coating resistant to the chemical etchant. Moreover, for objects that are to be etched using EChE, the coating may be an electrically non-conductive masking material or coating.

Coatings resistant to the chemical etching composition may be applied by any means known in the art, such as at least dipping, pouring, spraying, brushing, or rolling. Exemplary coatings resistant to the chemical etching compositions of the present invention include, for example, maskants from AC Products, such as ADCOAT AC-818.

Depending on the solids content of the selected coating, multiple applications of the coating may be necessary, allowing for sufficient drying time between applications. The coatings used are generally customized to protect the implantable device from the selected etchant while avoiding any harm to the underlying material of the object.

After each application, the coating may be allowed to cure in a manner which prevents damage to the preceding application, and/or which does not inhibit future applications. The term "cure", as used in connection with a cured coating, means that at least a portion of the components that form the coating are polymerized, cross-linked, or dried to form a hardened film. Curing or drying reactions to form the hardened film may be carried out under ambient conditions, or may be carried out at elevated temperatures, pressures, or in the presence of various gases. For example, the coating may comprise a solvent which may be evaporated to dry or cure the coating. The solvent evaporation may be accelerated by vacuum removal coupled with fresh air or inert gas supply. Depending upon the nature of the chosen coating, heat sources may be used to accelerate drying. Further, for certain coating chemistries, additional processing steps (imaging, hardening, fixing, etc.) may be necessary to make the coating fully resistant to the targeted etching solution.

The coating may be applied in a pattern that exposes the regions of the implantable device to be etched and covers the regions to be protected. Alternatively, the coating may be applied to a surface and patterned to remove those regions of the coating that are to be etched on the implantable device. Such removal may be via mechanical scribing and peeling, or by laser ablation, wherein a laser is utilized to remove or ablate the coating in specific regions or patterns. In both cases, a thickness of the coating may be matched to the characteristics of the scribing or laser ablation equipment. In general, the thinnest application that allows for full protection during the chemical etching step is desired, as thinner coatings require less drying time, less coating material, lower laser intensities, and less time stripping the coating after etching is complete. Moreover, for laser ablation processes, colorants or other additives may be added to the coating to improve the ablation process. The colorants and/or additives may be matched to the specific laser type and wavelength.

According to certain aspects, the coating may be a photoresist, wherein the photoresist may be applied to one or more surfaces, or portions thereof, of the device. A photoresist is a photosensitive coating that changes properties when exposed to light, either gaining or losing resistance to attack by an etchant or solvent in the areas exposed to electromagnetic radiation, most commonly in the UV light spectrum. The thickness and properties of the photoresist (e.g., positive or negative photoresist) may be matched to the equipment used for exposure of the pattern onto the photoresist.

While several methods for coating the surface of the implantable device have been described herein, other methods known in the art are within the scope of the present invention. Furthermore, more than one coating layer may be applied to the surface of the implantable device, wherein each coating layer may vary in thickness and identity of the coating material. As previously indicated, selection of the specific coating thickness and coating material may depend on at least the method of pattern generation to be used in future steps of the process.

The term "pattern generation" generally describes various methods and implementations used to remove a portion of the coating from the surface of the implantable device according to a specific pattern or design. The pattern may be preset or programmed into a computer (e.g., translated from CAD drawings) which directs the movements of the various devices used to remove the portion of coating and movements of the implantable device, either together or individually.

The patterned implantable device, whether produced through laser ablation, mechanical scribing and peeling, or by a photo resist process may be exposed to the alkaline chemical etching composition using any of dipping, rolling, brushing, or spraying. As indicated hereinabove, if the implantable device is contacted with the chemical etching composition in a bath, the device may be agitated while in the bath, or alternatively, the chemical etching solution may be provided as a flow of material (e.g., the device may be positioned in a stream of the chemical etching composition). Moreover, either or both of the implantable device and the chemical etching composition may be heated to a temperature in a range of from about 60° F. (about 15° C.) to about 280° F. (about 140° C.), such as from about 90° F. (about 32° C.) to about 250° F. (about 120° C.), or from about 150° F. (about 65° C.) to about 225° F. (about 110° C.), or from about 175° F. (about 80° C.) to about 200° F. (about 95° C.).

Alternatively, the patterned implantable device may be exposed to the electrochemical etching solution, i.e., the aqueous electrolyte solution, and may have a current passed therethrough as described hereinabove. Generally, the implantable device nay be exposed to the electrolyte solution through submersion in the solution.

The amount of material removed by the etching process, i.e., depth of etch, is generally less than about 10 mil (about 254,000 nm), such as less than about 5 mils (about 127,000 nm), or about 0.01 mils to about 5 mils (about 250 nm to about 127,000 nm) and may depend on the amount of exposure time to the chemical or electrochemical etching composition and depletion of the chemistry in the composition, e.g., after long exposure times. The upper limit of etch depth depends only on the time, temperature, and chemistry (e.g., ratio and/or concentrations of various components; recirculation or replacement of chemistry) of the etch reaction. For the electrochemical etch process, the etch depth may also depend on factors specific to the electric current generation and/or application, e.g., the voltage, current density, electrolyte gap, etc.

The rate of etching, i.e., rate of material removed, may depend on a combination of the proportion of chemical components to one another, the temperature, the surface being etched (i.e., type of metal), and/or the amount of agitation of the implantable device in the chemical etching composition, or the flow rate of the circulating etching solution (e.g., electrolyte or chemical etching solution). For example, according to certain aspects of the presently disclosed methods, the implantable device may be etched at a rate of 1.2 mil/hour (about 30,500 nm) for Grade 5 titanium, and at about 80% of that rate for Grade 2 titanium, when exposed to the chemical etch composition of the present invention. This rate can be greatly accelerated or slowed with changes in the exposure temperature (e.g., temperature of the implantable device, chemical etch composition, or both during the exposure reaction), and/or the concentration of components of the etch composition (e.g., greater concentration of the components). As indicated above, the rate of removal of material in the electrochemical process may also depend on factors specific to the electric current generation and/or application.

Nanoscale Surface Geometry

The nanoscale surface geometry imparted by the compositions and methods of the presently disclosed invention are distinguished from any geometry or pattern that may be applied using the maskants detailed above, or which may be provided on the substrate surface before the etching compositions are applied (e.g., certain implantable devices may comprise surface features provided by chemical or mechanical etching that are micrometers to millimeters in depth; see for example U.S. Pat. Nos. 5,258,098, 5,507,815, and 6,193,762). Moreover, the nanoscale surface geometry or topography is different from the "depth of etch" described herein, where longer etch times may remove greater amounts of the metal surface (i.e., greater depth of the etch). Longer etch times may be useful to remove artifacts of manufacture, such as support structures formed during 3D manufacture of the implantable device, or islands left behind during laser manufacture of an implantable device, or to reduce debris from the implantable device surfaces, such as artifacts of the additive manufacturing process, e.g., powder, particles, granules, etc., that were not completely melted or completely sintered during the additive building. Debris may also include external debris such as dirt or other artifacts of handling.

Once etching is complete, the implantable device may be rinsed clean of all residual etchant. According to certain aspect, the implantable device is substantially free or totally free of residual etchant. As indicated above, according to certain aspects, an alkaline etched surface or device may be rinsed with deionized water and exposed to a nitric flash as described hereinabove.

Surface manipulation of an implantable device is typically performed to create surface features with dimensions (X, Y and Z) in the nanometer range, such as in a size range of 20-2,000 nm, although one or more of the dimensions could be much larger, such as with a long narrow ridge of material. mesenchymal stem cells If the implantable device was coated on a portion thereof with a maskant or etch resistant coating, the maskant may be removed by placing the device in a bath of stripping solution (a solvent matched to the coatings) to remove all remaining coating material. According to certain aspect, the implantable device is substantially free or totally free of residual maskant. Alternatively, a wet blast process consisting of a high-pressure spray of a stripping solution could be used in place of the stripping solution to mechanically and chemically remove the coating from the object. After the remaining coating is removed ("stripping"), the implantable device may be thoroughly pressure-washed or rinsed and dried in preparation for any required final surface treatments, or sterilization prior to packaging for future use.

The chemical and/or electrochemical etching compositions and methods disclosed herein may provide a regular repeating, though non-identical, pattern having nanoscale geometry on a substrate surface. This pattern is an outcome of the chemical or electrochemical reactions of the inventive compositions disclosed herein and is not the result of a specifically applied pattern. Moreover, while any two areas of the etched surface may have the same surface roughness and topographical features, and thus may appear to have a regular repeating pattern, these patterns are not identical. While the etch depth is indicated above to be on the micrometer scale (e.g., generally less than 1 mil or 25.4 micrometers), the chemical or electrochemical etching compositions provide a geometry on the surface of the device that is on the nanometer scale (i.e., surface roughness and topographical features, nanoscale topography).

These surfaces have been found to improve osseointegration of bone contacting implantable devices. Without wishing to be bound by one particular theory, the nanoscale geometry may provide pores into which osteoblasts and supporting connective tissue can migrate. Thus, the compositions and methods disclosed herein provide an improved surface on an osteoid implant, such as on a surface that may contact an adjoining surface (i.e., bone), and may help to promote bone growth, fusion, and healing responses. Such implants can include any bone contacting device known in the medical and dental fields, such as a bone fixative device or dental implant. For example, surgical bone fixation devices such as screws, staples, rods, wires, and plates. The irregular surface into which the bone grows creates a natural joinder between the bone and the implant, which maximizes the surface area of the joined element and improves the structural stability and functional connection therebetween.

These surfaces have also been found to improve biocompatibility of tissue contacting implantable devices. For example, stents and valves that have the nanoscale surface geometry reduce the incidence of restenosis. Restenosis occurs when smooth muscle cells in the blood aggregate into clumps and cause the stent to become occluded. While drug-eluting coatings have been used to prevent clumping, recent data has found that these coatings are not a satisfactory solution (i.e., coated stents have been shown to cause blood clots several years after installation). A patient receiving a coated stent must use blood thinners to prevent formation of blood clots that may dislodge from the region of the stent and cause stroke or heart attack. Restenosis of a stent may be largely determined by whether the first layer of cells to grow on the surface of a stent are endothelial cells or smooth muscle cells.

The nanoscale surface geometry of the present invention preferably selects endothelial cells (e.g., from the blood stream) to grow on the inside surface of the stent or stent cover compared to other cell types (e.g., smooth muscle cells). Endothelial cells, as opposed to smooth muscle cells, may 'recognize' the surface structure by pattern matching and adhere. This pattern recognition step is a key element in many molecular biology processes. The implantable devices having nanoscale surface geometry, and the methods and compositions useful for forming the geometry, take advantage of this native molecular biological process to influence the adherence of one type of cell, e.g. endothelial cells, in preference to other types, e.g. smooth muscle cells. Thus, surface nanostructures may be used to selectively enhance adhesion of endothelial cells over smooth muscle cells.

The nanoscale surfaces provided by the compositions and methods disclosed herein are improved over those formed by the prior art acid etch methods. That is, when included on an implant, they demonstrate improved osseointegration and/or biocompatibility of the implant when compared to prior art implants having surfaces formed using acid etch methods. Prior art solutions for improving biocompatibility used coatings, such as nanoporous hydroxyapatite or nanoporous aluminum oxide, to provide improved endothelialization. However, preclinical studies have shown variability regarding the effectiveness of stents coated with nanoporous materials, and nanoparticle debris ejected from the stent surface has been observed. This debris could provoke inflammation and subsequent restenosis.

Accordingly, the present invention provides an improved implantable device comprising a body with at least one surface having a defined three-dimensional pattern created by the etching compositions and methods of the present invention.

Implantable Devices

The implantable devices of the presently disclosed invention may be any device that is either partly or totally introduced, surgically or medically, into the body of a manual, such as a human, dog, cat, cow, pig, etc., and is intended to remain there after the procedure.

Exemplary devices that may comprise the nanoscale surface geometry imparted by the compositions and methods of the presently disclosed invention include medical devices that are tissue contacting, such as an (auxiliary) artificial heart, an artificial valve, a stent, and a pacemaker. In the case of the (auxiliary) artificial heart, examples of the component of the device include a pump casing, an impeller, a shaft constituting the impeller, a rotor and a fin, and an inlet port and an outlet port communicating with the pump casing. The implantable device may be implanted to replace or repair a part or portion thereof that has worn-out, such as a heart valve or replacement joint, or may be used to ameliorate a condition of the mammal that may benefit from insertion of the implantable device such as a stent. The implantable device may also be useful for sensing a physiological response in vivo or to actuate physiological organs, such as an implantable cardiac defibrillator, pacemaker, cochlear implant, implanted bladder stimulator, implantable wireless pressure sensor, etc.

Exemplary devices also include any medical or dental implant for connection to, or positioning adjacent, living bone of a patient. For example, surgical bone fixation devices such as screws, staples, rods, and plates, and implants including at least medical implants such as spinal implants, limb prostheses, portions of a joint replacement device, cochlear prostheses, and dental implants.

Restorative implant dentistry generally involves the surgical restoration of one or more teeth in a patient's mouth using an osseointegrative dental implant or anchor that supports a prosthetic tooth (e.g., a porcelain crown), an implant-supported bridge or an implant-supported denture. Dental implants have traditionally been fabricated as a bone-anchoring pin or screw formed from a known osseointegrative material, such as pure titanium or a titanium alloy. The bone-anchoring portion of the pin or screw is typically configured to extend into an osteotomy formed within the alveolar bone (either the maxilla or the mandible) of a patient. Biological healing and bone tissue growth around the surgical site eventually results in osseointegration (i.e., permanent fixation) of the implant with the living bone tissue surrounding the osteotomy and the implant. Other portions of the implant typically extend through the gingiva into the oral cavity to support one or more prosthetic teeth.

Accordingly, the present invention further provides dental implants comprising a body with at least one surface having a defined three-dimensional pattern created by the chemical or electrochemical etching compositions and methods of the present invention. The at least one surface having the etched pattern is positioned in contact with living bone of a patient, such as an alveolar bone. For example, the dental implant may include a core or anchor portion formed of titanium, and a head portion that extends from the anchor portion and has an abutment interface. The anchor portion generally includes the surface having a defined three-dimensional pattern disposed about the portion that interfaces with the alveolar bone. After implantation of the implant, such as by screwing or press-fitting the core into the bone (i.e., the osteotomy), bone tissue may osseointegrate into the surface having the defined three-dimensional pattern to anchor the implant in position within the surrounding bone. The head portion may provide an attachment point for the additional portions of the implant (e.g., a porcelain crown or denture).

As described, the anchor portion of the dental implant is positioned within the alveolar bone by press fitting or screwing. As such, the surface of the anchor portion of the dental implant may include either a smooth cylindrical form which is press-fit into a drilled osteotomy, or a threaded form which is threaded into a threaded or unthreaded osteotomy prepared using a bone drill, a bone tap and/or other specialized tools. The geometry of a threaded implant is typically such that it can be inserted into the osteotomy and firmly secured to the surrounding bone tissue via one or more threads which advance into the osteotomy. In a two-stage dental implant, as described above, the anchor and head portions may include addition portions, and may be formed of solid metal such as titanium or may be coated with a layer of titanium.

Alternative dental implants include single-stage implants, wherein the tooth or prosthetic is integral with the anchor portion of the implant. In such a case, the entire implant may be formed of a ceramic or other appropriate material for a tooth or prostheses, and the anchor portion may include a coating or layer of solid metal such as titanium on a surface thereof, wherein the metal coating includes the defined three-dimensional pattern.

The present invention farther provides medical implants such a spinal implant, wherein the implant has a body comprising a surface and connections sized and shaped for placement into an intravertebral disc space. The surface has a defined three-dimensional pattern created by the chemical or electrochemical etching compositions and methods of the present invention. The implant thus provides a surface area of bone-contacting features that allow for and encourage in-growth of bone and proteinaceous materials and biological attachment to a biocompatible material i.e., integration. The three-dimensional surface morphology may, incorporate overlapping patterns of features in two dimensions as well as different and independent dimensional depths for each of the features (etched to microscale depths with nanoscale features).

Other exemplary implants include at least prosthetic devices or implants intended for repair of a traumatic bone injury. For example, the chemical or electrochemical etching compositions and methods of the present invention can be applied to at least one surface of an implant intended for connection or replacement of any type of long bone, including the femurs, tibias and fibulas of the legs, the humeri, radii and ulnas of the arms, metacarpals and metatarsals of the hands and feet and the phalanges of the fingers and toes. Implants formed by these methods can be used in the field of prosthetic surgery, for example in case of hip, knee, ankle, shoulder, elbow or finger prostheses or joint replacement. Moreover, implants formed by these methods may find use in craniofacial prosthesis such as an artificial ear (ear prosthesis), maxillofacial reconstruction, eye (orbital prosthesis), or nose (nose prosthesis), bone anchored hearing conduction amplification (i.e., bone anchored hearing aid), and cyborg antenna or "eyeborg," which is a device that is implanted in the skull to perceive color through sound waves (sound conduction through bone).

It is generally believed that the three-dimensional surface of the implantable device determines its ultimate ability to integrate into the surrounding living bone. Without being limited by theory, it is hypothesized that the cumulative effects of at least implant composition, implant surface energy, and implant surface topography play a major role in the biological response to, and osseointegration of, the implantable device.

Various implant body shapes may be generated to allow for implantation at various body sites and through various access paths. The structures and surfaces are designed to work in concert to preserve bone structures, and to provide for sufficient bioactivity in each respective location. For example, when the implantable device is a spinal implant, the device may provide stability within the disc space and the graft containment axial column, and the shapes and textures of the bioactive surfaces may vary based on the implant insertion path, location within the disc space, and frictional characteristics of the surfaces. Exemplary spinal implants include those shown in U.S. Pat. Nos. 8,262,737; 8,496,710; 8,585,765; and 10,111,753.

Implantable devices according to the presently disclosed invention may be formed by any of the manufacturing processes known to one of skill in the art. For example, the implantable device may be formed by a subtractive manufacturing process, such as by direct machining, or may be formed by an additive manufacturing process.

As understood by someone skilled in the art, the term "additive manufacturing" contemplates a manufacturing technology as defined in the international standard ASTM 2792-12. It refers to a process of making useful three-dimensional (3D) objects through a series of sequential steps, forming the shape of the object one layer at a time. Additive manufacturing processes include, but are not limited to, three-dimensional printing (3DP) processes, laser-net-shape manufacturing, direct metal laser sintering (DMLS), direct metal laser melting (DMLM), plasma transferred arc, freeform fabrication, direct digital manufacturing, layered manufacturing, and rapid prototyping. The additive manufacturing method may be selected from, but is not limited to, stereolithography, mask stereolithography, mask projection stereolithography, polymer jetting, scanning laser sintering (SLS), scanning laser melting (SLM), electronic beam melting (EBM), and fused deposition modeling (FDM).

Additive manufacturing technologies comprise processes that create objects by juxtaposition of volume elements according to a pre-determined arrangement that can be defined in a computer aided design file (CAD). Such juxtaposition is the result of sequential operations such as budding a material layer on top of a previously obtained material layer and/or juxtaposing a material volume element next to a previously obtained volume element. The 3D CAD models used to define the implantable devices may be based on standard 3D designs or may be based on 3D representations of the implantation site of the device (i.e., device is specific to a patient). While certain specific methods and manufacturing processes have been mentioned herein, such disclosure should not be understood to limit the methods of forming the implantable devices or surfaces thereof disclosed herein.

Moreover, the particular etchant reaction conditions and/or maskant utilized for a given attachment surface may be dictated by the base metal utilized for the implant. While a titanium implant is contemplated as the best mode of practice in the invention, it is to be specifically understood that any base metal etchable with the alkaline compositions disclosed herein may be utilized as the implanted material. A change in the base metal would necessitate a change in the maskant and etchant reaction conditions. No limitation is to be inferred from the selection of titanium, or a specific alloy of titanium, in the detailed description.

ASPECTS OF THE INVENTION

The following aspects are disclosed in this application:

Aspect 1. An alkaline composition for etching a nanoscale surface geometry on a metal surface, the composition comprising: a metal hydroxide; an amine; and one or more chelating agents.

Aspect 2. The composition according to Aspect 1, further comprising one or both of iron (Fe) and a component metal of the metal surface.

Aspect 3 The composition according to Aspects 1 or 2, wherein amine is an alkanolamine.

Aspect 4. The composition according to any one of Aspects 1 to 3, wherein the one or more chelating agents comprise a gluconate.

Aspect 5. The composition according to any one of Aspects 1 to 4, wherein the composition comprises iron at 0.1 ppm to 10,000 ppm.

Aspect 6. The composition according to any one of Aspects 1 to 5, wherein the metal surface comprises a titanium or titanium alloy surface, and the component metal of the metal surface comprises dissolved titanium at 0.1 ppm to 100,000 ppm.

Aspect 7. The composition according to any one of Aspects 1 to 6, wherein the composition is an aqueous composition.

Aspect 8. The composition according to any one of Aspects 1 to 7, wherein the composition comprises 5 to 75 wt. % of the metal hydroxide; 0.1 to 40 wt. % of the amine; 0.1 to 40 wt. % of the one or more chelating agents; and 0.1 to 10,000 ppm iron (Fe).

Aspect 9. The composition according to any one of Aspects 1 to 8, comprising: 18 to 30 wt. % of the metal hydroxide; 2 to 10 wt. % of the amine; 2 to 10 wt. % of the one or more chelating agents; 70 to 180 ppm iron (Fe); and 5 to 7,000 ppm dissolved titanium.

Aspect 10. The composition according to any one of Aspects 1 to 9, wherein the device is a body implantable device.

Aspect 11. The composition according to Aspect 10, wherein the body implantable device is a bone-contacting device and the nanoscale surface geometry enhances osseointegration when the bone-contacting device is implanted adjacent bone, or wherein the body implantable device is a tissue-contacting device and the nanoscale surface geometry enhances endothelial attachment and proliferation when the tissue-contacting device is implanted adjacent tissue.

Aspect 12. A method for etching a nanoscale surface geometry in at least one surface of an implantable device, the method comprising: submersing the implantable device in an aqueous electrolyte solution, wherein the aqueous electrolyte solution comprises 0.01M to 10M of one or more metal salts, wherein the one or more metal salts are selected from the group comprising NaBr, NaCl, NaF, KBr, KCl, NaNO$_3$, and KF; and passing an electric current of 5 Amps/in$^2$ to 100 Amps/in$^2$ through the electrolyte solution between a cathode and an anode, wherein the implantable device acts as the anode or is attached to the anode.

Aspect 13. The method according to Aspect 12, wherein the one or more metal salts comprise NaCl, NaBr, and NaF.

Aspect 14. The method according to Aspect 12 or 13, wherein the one or metal salts comprise about 3 M NaCl, about 1.2 M NaBr, and about 0.6M NaF.

Aspect 15. The method according to Aspect 12, wherein the one or more metal salts comprise NaCl, NaNO$_3$, and NaF.

Aspect 16. The method according to Aspect 12 or 13, wherein the one or metal salts comprise about 3 M NaCl, about 1.2 M NaNO$_3$, and about 0.6M NaF.

Aspect 17. The method according to any one of Aspects 12 to 16, wherein the aqueous electrolyte solution is circulated.

Aspect 18. A method for etching a nanoscale surface geometry on at least one surface of a titanium device, the method comprising contacting the at least one surface of the titanium device with the alkaline composition according to any one of Aspects 1 to 11 at a temperature of 15° C. to 140° C. for 1 minute to 100 hours.

Aspect 19. The method according to Aspect 18, wherein the titanium device is contacted with the aqueous alkaline composition at the temperature of 80° C. to 95° C. for 10 to 60 minutes.

Aspect 20. The method according to Aspect 18 or 19, wherein before the step of contacting the at least one surface of the titanium device with the alkaline composition, the method further comprises: applying a coating that resists chemical etchants to at least a portion of the implantable device.

Aspect 21. The method according to Aspect 20, further comprising, after contacting, the at least one surface of the implantable device with the aqueous alkaline composition: stripping the coating from the implantable device.

Aspect 22. The method according to Aspect 18 to 21, further comprising, after contacting the at least one surface of the titanium device with the aqueous alkaline composition, exposing the at least one surface to a 5% to 60% (v/v) solution of nitric acid for up to 5 minutes at 15° C. to 32° C.

Aspect 23. The method of Aspect 18 to 21, further comprising, after contacting the at least one surface of the titanium device with the aqueous alkaline composition, exposing the at least one surface to a 5% to 15% (v/v) solution of nitric acid for up to 10 seconds to 120 seconds at 15° C. to 32° C.

Aspect 24. The method according to any one of Aspects 18 to 23, wherein the titanium device is an implantable bone-contacting device, and wherein the nanoscale surface geometry enhances osseointegration when the bone-contacting device is implanted adjacent bone.

Aspect 25. The method according to any one of Aspects 18 to 23, wherein the titanium device is an implantable tissue-contacting device; and the nanoscale surface geometry enhances endothelial attachment and proliferation when the tissue-contacting device is implanted adjacent tissue.

Aspect 26. A titanium device for implantation within a body of a patient, the device comprising at least one surface having nanoscale surface geometry formed by contacting the at least one surface with any of the alkaline compositions of Aspect 1 to 11 according to any of the methods of Aspects 12 to 25.

Aspect 27. A titanium device for implantation within a body of a patient, the device comprising at least one surface having nanoscale surface geometry formed by contacting the at least one surface with any of the alkaline compositions of Aspect 1 to 11 at a temperature of 15° C. to 140° C. for 1 minute to 100 hours, followed by exposing the at least one surface to a 5% to 60% (v/v) solution of nitric acid for up to 5 minutes at 15° C. to 32° C.

Aspect 28. The device according to Aspect 27, wherein the device is an implantable bone-contacting device, and wherein the nanoscale surface geometry enhances osseointegration when the bone-contacting device is implanted adjacent bone.

Aspect 29. The device according to Aspect 27 or 28, wherein the device is an implantable bone-contacting device such as a spinal implant, a dental implant, a prosthetic implant such as a limb prosthesis, a cochlear implant such as a cochlear prosthesis, or a surgical bone fixation device such as a screw, staple, rod, or plate.

Aspect 30. The device according to Aspect 28 or 29, wherein the osseointegration is at least 50% greater on the at least one surface having the nanoscale surface geometry than on an untreated surface.

Aspect 31. The device according to Aspect 27, wherein the device is an implantable tissue-contacting device, and the nanoscale surface geometry enhances endothelial attachment and proliferation when the tissue-contacting device is implanted adjacent tissue

EXAMPLES

Example 1. Chemical Etching of a Titanium Surface

An exemplary chemical etching composition for the chemical dissolution of a titanium surface according to certain aspects of the presently disclosed invention include constituents and amounts as shown in Table I.

TABLE I

| Component | Range | Set-Point |
|---|---|---|
| Iron (Fe) | 0.1-500 ppm | 70-180 ppm |
| Titanium (Ti) | 0-100,000 ppm | 0.1-7,000 ppm |
| Metal Hydroxide | 5-75 wt. % | 18-30 wt. % |
| Amine | 0.1-40 wt. % | 2-10 wt. % |
| Chelating agent | 0.1-40 wt. % | 2-10 wt. % |

* When the total metals content equals 100 ppm, it may be provided by either the iron and/or the titanium, i.e., if 100 ppm iron is included, the titanium may be absent, and vice versa.

Temperature ranges for the above solutions are from about 15° C. to about 140° C., such as about 80° C. to about 95° C., for time periods of up to 100 hours, such as at least 1 minute to 10 hours, or from 10 minutes to 60 minutes.

Example II: Chemical Etching of an Aluminum Surface

An exemplary chemical etching composition for the chemical dissolution of an aluminum surface according to certain aspects of the presently disclosed invention include constituents and amounts as shown in Table II.

TABLE II

| Component | Range | Set-Point |
| --- | --- | --- |
| Iron (Fe) | 0-500 ppm | 70-180 ppm |
| Aluminum (Al) | 0-100,000 ppm* | 100-7,000 ppm |
| Metal Hydroxide | 5-75 wt. % | 18-30 wt. % |
| Amine | 0.1-40 wt. % | 2-10 wt. % |
| Chelating agent | 0.1-40 wt. % | 2-10 wt. % |

*When the total metals content equals 100 ppm, it may be provided by either the iron and/or the aluminum, i.e., if 100 ppm iron is included, the aluminum may be absent, and vice versa.

Temperature ranges for the above solutions are from about 15° C. to about 140° C., such as about 80° C. to about 95° C., for time periods of up to 100 hours, such as at least 1 minute to 10 hours, or from 10 minutes to 60 minutes.

Example III: Electrochemical Etching of a Metal or Metal Alloy Surface

Desired surface characteristics on various metals and metal alloys can also be achieved using an electrolyte solution that includes a mixture of one or more of sodium chloride (NaCl), potassium chloride (KCl), calcium chloride ($CaCl_2$), magnesium chloride ($MgCl_2$), ammonium chloride ($NH_4Cl$), dibasic sodium phosphate ($Na_2HPO_4$), monobasic sodium phosphate ($NaH_2PO_4$), monobasic potassium phosphate ($KH_2PO_4$), dibasic potassium phosphate ($K_2HPO_4$), sodium sulfate ($Na_2SO_4$), potassium sulfate ($K_2SO_4$), ammonium sulfate (($NH_4)_2SO_4$), sodium nitrate ($NaNO_3$), potassium nitrate ($KNO_3$), ammonium nitrate ($NH_4NO_3$), potassium nitrite ($KNO_2$), potassium bromide (KBr), sodium bromide (NaBr), ammonium bromide ($NH_4Br$), calcium bromide ($CaBr_2$), magnesium bromide ($MgBr_2$), sodium fluoride (NaF), potassium fluoride (KF), lithium fluoride (LiF), magnesium fluoride ($MgF_2$), calcium fluoride ($CaF_2$). Preferred electrolytes include NaCl, $NaNO_3$, and NaF. Typically, the water-soluble inorganic compound is present in the electrolyte solution at a concentration of about 0.01M to saturation, such as from about 0.05M to about 10M, or from a concentration of about 0.05M to about 5M, or from a concentration of about 0.05M to about 3M.

For example, in an exemplary embodiment, from 0.5M to 10M of each of NaCl, $NaNO_3$, and NaF are included in water to form the aqueous electrolyte solution. A specific exemplary embodiment is shown in Table I below, which is suitable for the electrochemical dissolution of a titanium surface according to certain aspects of the presently disclosed invention.

TABLE III

| Component | Range | Preferred Set-Point |
| --- | --- | --- |
| NaCl | 0.01-6.5M | 3.0M |
| $NaNO_3$ | 0.01-8.5M | 1.2M |
| NaF | 0.01-0.5M | 0.6M |

Example IV: Osseointegration of a Titanium Surface Having a Nanoscale Surface

Background of Selected Markers: Osteogenic differentiation is a continuous process characterized by the rise and fall of several proteins. The proteins analyzed herein characterize early (alkaline phosphatase; ALP), lifetime (osteopontin; OPN) and late (osteocalcin; OCN) osteoblast markers. The process of osteoblast differentiation begins with mesenchymal stem cells progressing to an intermediate progenitor capable of undergoing either osteogenesis or chondrogenesis and expressing ALP. These intermediate progenitors that commit to an osteogenic lineage, now termed preosteoblasts, increase the expression of ALP and OPN. As the preosteoblast progresses to a mature osteoblast the expression of OCN is increased. The osteoblast will eventually mature further and begin transitioning to an osteocyte or undergo apoptosis. This mature osteoblast state is characterized by a decrease in ALP and once the osteoblast differentiates to an osteocyte the expression of OCN is decreased as well (Baek, W, et al., *Positive Regulation of Adult Bone Formation by Osteoblast-Specific Transcription Factor Osterix*. J. Bone Miner. Res. (2009) 24(6) 1055-65, Zhang, C, et al., *Tanscriptional regulation of bone formation by the osteoblast-specific transcription factor Osx*. Journal of Orthopedic Surgery and Research (2010) 5(1):1; Tu, Q, et al., *Osterix Overexpression in Mesenchymal Stem Cells Stimulates Healing of Critical-Sized Defects in Murine Calvarial Bone*. Tissue Eng. (2007) 13(10):2431-40). The only matrix protein produced by a preosteoblast, osteoblast and osteocyte is OPN.

In vivo evaluations have revealed that both ALP and OCN are present during fracture healing. In these evaluations both ALP and OCN production is highest in healing bone fractures at 8 weeks post fracture (Leung, K, et al., *Plasma bone-specific alkaline phosphatase as an indicator of osteoblastic activity*. Bone & Joint Journal (1993) 75-B(2):288-92: Herrmann, M, et al., *Different Kinetics of Bone Markers in Normal and Delayed Fracture Healing of Long Bones* Clinical Chemistry (2002) 48(12):2263-6). Furthermore, ALP and OCN have been used for in vitro evaluation of the potential for a synthetic material to promote bone formation in vivo. Increased ALP and OCN in vitro have been demonstrated to be associated with synthetic graft success in vivo (Borden, M, et al., *Tissue-engineered bone formation in vivo using a novel sintered polymeric microsphere matrix*. J Bone Joint Surg Br. (2004) 86(8):1200-8). Similar evaluations using titanium mesh have correlated in vitro ALP and OPN with in vivo success (Bancroft, G, et al., *Fluid flow increases mineralized matrix deposition in 3D perfusion culture of marrow stromal osteoblasts in a dose-dependent manner*. Proc. Natl. Acad. Sci. (2002) 99(20):12600-5).

Samples of titanium substrates were treated with the alkaline compositions of the presently disclosed invention as follows: Sample A was treated with the alkaline composition without a nitric flash, Sample B was treated with the alkaline composition with a nitric flash, Sample C is a control sample of a medical implant surface currently on the market treated as Sample B (alkaline composition with a nitric flash), and Control is an untreated sample of the currently available medical implant surface. The nitric flash is a short treatment with a dilute solution of nitric acid, specifically, a 90 second exposure to a 10-12% solution of nitric acid at room temperature.

Figure 2A:
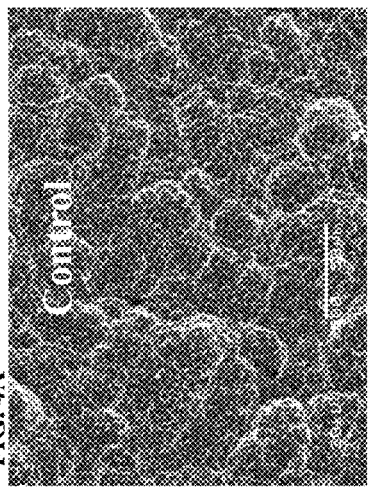
Figure 2B:
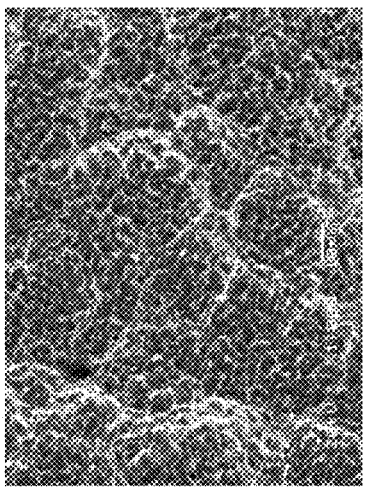
Figure 2C:
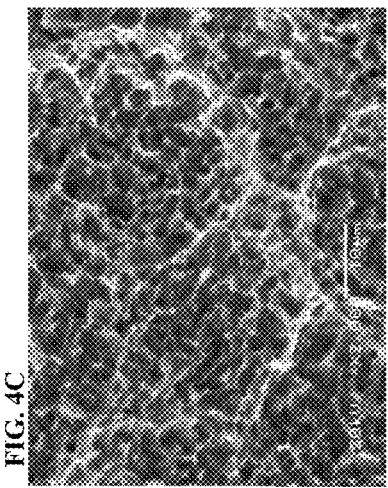
Figure 3A:
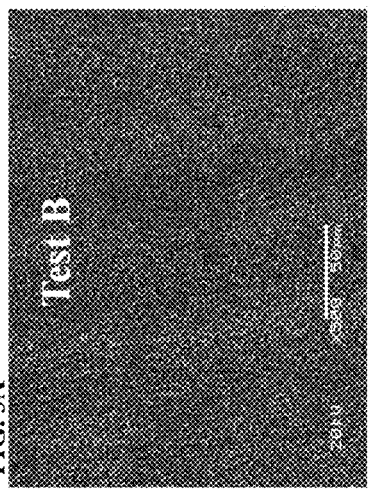
Figure 3B:
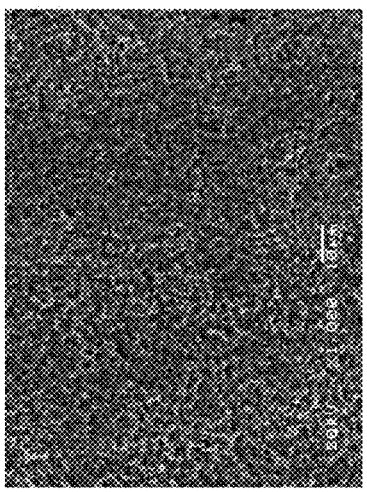
Figure 3C:
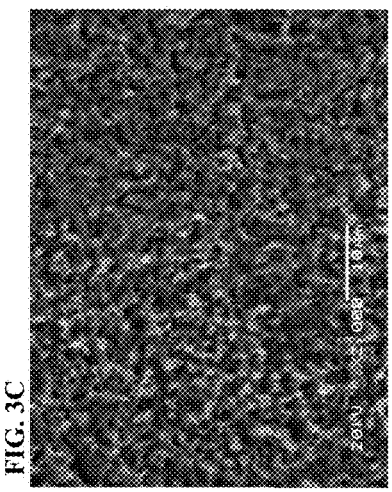
Figure 4A:
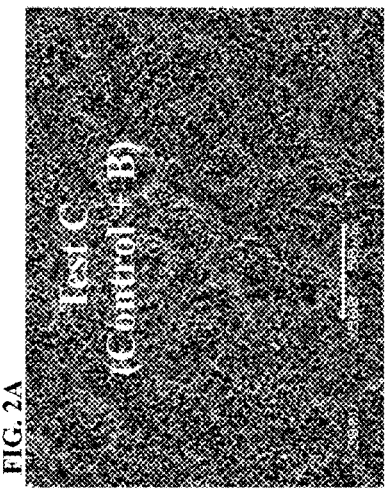
Figure 4B:
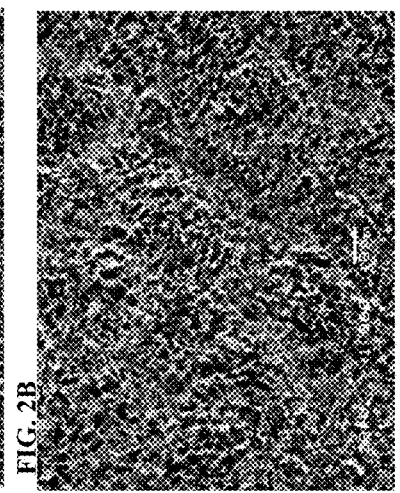
Figure 4C:
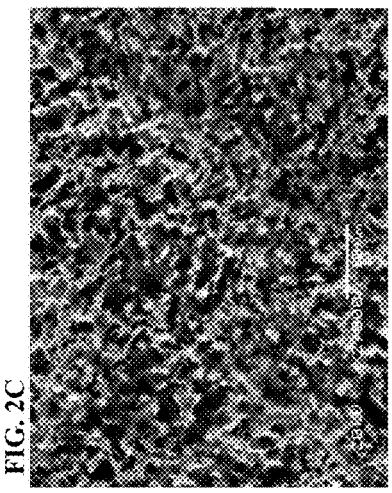

Shown in FIGS. 2A-4C are surface scanning electron microscopy images of Samples C, B, and the control sample, respectively. Samples in FIGS. 2A, 3A, and 4A are 500× magnification, samples in FIGS. 2B, 3B, and 4B are 1000× magnifications, and samples in FIGS. 2C, 3C, and 4C are at 2000× magnification. With specific reference to FIGS. 4A-4C, the control sample is shown to be substantially absent nanoscale geometry, and rather can be seen to have micrometer sized features.

The expression of OPN, ALP, and OCN at 7 days and 14 days of osteoblast growth on each of the Samples A, B, C and the control sample was tested. With reference to FIGS.

1A-1C, all four test samples as described above supported the expected significant rise in the production of OPN in the osteoblasts across the two growth time points of 7 days and 14 days. With specific reference to FIG. 1A, osteoblasts growing on the control sample (ctrl) demonstrated significantly more OPN expression than those growing on any other surface. Furthermore, osteoblasts growing on Sample C demonstrated a significant increase in OPN expression as compared to those growing on Sample A.

Figure 1B:
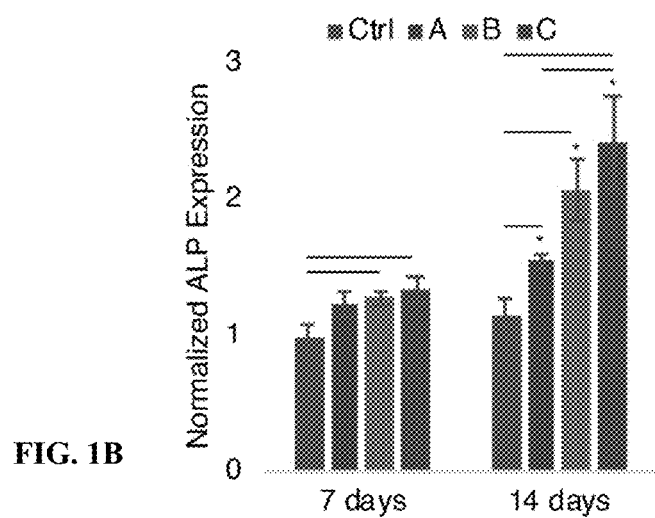

As shown in FIG. 1B, the early marker ALP showed a significant increase in expression across the two time points from cells grown on Samples A, B, and C, but not for those grown on the control sample. Furthermore, osteoblasts grown on Samples B and C demonstrated significant increases in ALP expression at both 7 and 14 days when compared to those grown on the control sample. Finally, osteoblasts grown on Sample C demonstrated significant increases in ALP expression as compared to those grown on Sample A at 14 days.

Figure 1C:
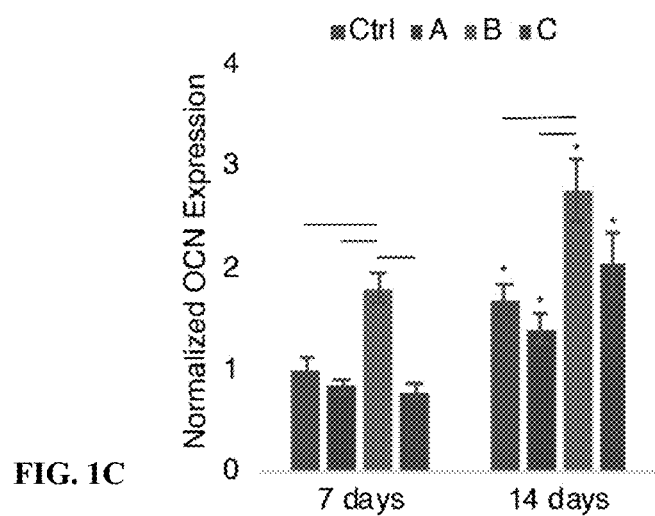

With reference to FIG. 1C, all four samples supported the expected significant increase in OCN expression across the two time points. Osteoblasts grown on Sample B demonstrated significantly more OCN expression at 7 days in comparison to osteoblasts grown on all other samples. Similarly, cell grown on Sample B demonstrated significantly more OCN expression at 14 days when compared with those grown on the control sample and Sample A.

Conclusions: Taken together, the trends identified by expression of the three markers point to Sample B demonstrating rapid osteogenic differentiation, followed by Sample C. For example, a titanium alloy surface etched with an alkaline etching composition according to methods of the present invention demonstrated a 50% increase in osteogenic differentiation over the control sample.

While the presently disclosed invention has been described in detail, it should be appreciated by those skilled in the art that various modifications and alternations and applications could be developed in light of the overall teachings of the disclosure. Accordingly, the particular systems and methods disclosed are meant to be illustrative only and not limiting as to the scope of the invention.

What is claimed is:

1. An alkaline composition for etching a nanoscale surface geometry on a surface of a body implantable device, the composition comprising:
   18 to 30 wt. % of a metal hydroxide; at least 0.01 wt. % of an amine; 2 to 10 wt. % of one or more chelating agents; and component metals of the surface,
   wherein the surface of the body implantable device comprises titanium or a titanium alloy, and the component metals of the surface comprise titanium at 0.1 ppm to 100,000 ppm, and
   wherein the body implantable device is a bone-contacting device and the nanoscale surface geometry enhances osseointegration when the bone-contacting device is implanted adjacent bone, or
   wherein the body implantable device is a tissue-contacting device and the nanoscale surface geometry enhances endothelial attachment and proliferation when the tissue-contacting device is implanted adjacent tissue.

2. The composition of claim 1, wherein the amine is an alkanolamine included in the composition at 2 wt. % to 10 wt. %.

3. The composition of claim 1, wherein the one or more chelating agents comprise a gluconate.

4. The composition of claim 1, wherein the composition comprises iron at 0.1 ppm to 10,000 ppm.

5. The composition of claim 1, comprising dissolved titanium at 7 ppm to 7,000 ppm.

6. An aqueous alkaline composition for etching a nanoscale surface geometry on a metal surface, the composition comprising:
   18 to 30 wt. % of a metal hydroxide;
   0.1 to 40 wt. % of an alkanolamine;
   2 to 10 wt. % of a gluconate, and
   0.1 ppm to 100,000 ppm dissolved titanium.

7. An aqueous alkaline composition for etching a nanoscale surface geometry on a metal surface, the composition comprising:
   18 to 30 wt. % of the metal hydroxide;
   2 to 10 wt. % of the alkanolamine;
   2 to 10 wt. % of a gluconate;
   70 to 180 ppm iron (Fe); and
   5 to 7,000 ppm dissolved titanium.

8. A method for etching a nanoscale surface geometry on at least one surface of a titanium device, the method comprising contacting the at least one surface of the titanium device with the aqueous alkaline composition of claim 1 at a temperature of 15° C. to 140° C. for 1 minute to 100 hours.

9. The method of claim 8, wherein the titanium device is contacted with the aqueous alkaline composition at the temperature of 80° C. to 95° C. for 10 to 60 minutes.

10. The method of claim 8, further comprising, after contacting the at least one surface of the titanium device with the aqueous alkaline composition, exposing the at least one surface to a 5% to 60% (v/v) solution of nitric acid for 5 minutes at 15° C. to 32° C.

11. The method of claim 8, further comprising, after contacting the at least one surface of the titanium device with the aqueous alkaline composition, exposing the at least one surface to a 5% to 15% (v/v) solution of nitric acid for 10 seconds to 120 seconds at 15° C. to 32° C.

12. The method of claim 8, wherein the titanium device is an implantable bone-contacting device, and wherein the nanoscale surface geometry enhances osseointegration when the bone-contacting device is implanted adjacent bone.

13. The method of claim 8, wherein the titanium device is an implantable tissue-contacting device, and the nanoscale surface geometry enhances endothelial attachment and proliferation when the tissue-contacting device is implanted adjacent tissue.

14. A method for etching a nanoscale surface geometry on at least one surface of an implantable device, the method comprising:
   applying a coating that resists chemical etchants to at least a portion of the implantable device; and
   contacting the at least one surface of the implantable device with the aqueous alkaline composition of claim 1.

15. The method of claim 14, wherein the implantable device is contacted with the aqueous alkaline composition at a temperature of 80° C. to 95° C. for 10 to 60 minutes.

16. The method of claim 14, further comprising, after contacting the at least one surface of the implantable device with the aqueous alkaline composition:
   stripping the coating from the implantable device.

17. A method for etching a nanoscale surface geometry on at least one surface of a titanium device, the method comprising contacting the at least one surface of the titanium device with the aqueous alkaline composition of claim 7 at a temperature of 15° C. to 140° C. for 1 minute to 100 hours.

18. The method of claim 17, further comprising, after contacting the at least one surface of the titanium device with the aqueous alkaline composition, exposing the at least one surface to a 5% to 60% (v/v) solution of nitric acid for 5 minutes at 15° C. to 32° C.

19. A method for etching a nanoscale surface geometry on at least one surface of a titanium device, the method comprising contacting the at least one surface of the titanium device with the aqueous alkaline composition of claim 6 at a temperature of 15° C. to 140° C. for 1 minute to 100 hours.

20. The method of claim 19, further comprising, after contacting the at least one surface of the titanium device with the aqueous alkaline composition, exposing the at least one surface to a 5% to 60% (v/v) solution of nitric acid for 5 minutes at 15° C. to 32° C.

\* \* \* \* \*